(12) United States Patent
Black

(10) Patent No.: US 11,602,406 B1
(45) Date of Patent: *Mar. 14, 2023

(54) SYSTEM AND METHOD FOR RAPIDLY ACCESSING AN IMPROVED TOURNIQUET

(71) Applicant: Bryan Black, Arlington, TX (US)

(72) Inventor: Bryan Black, Arlington, TX (US)

( * ) Notice: Subject to any disclaimer, the term of this patent is extended or adjusted under 35 U.S.C. 154(b) by 165 days.

This patent is subject to a terminal disclaimer.

(21) Appl. No.: 17/101,795

(22) Filed: Nov. 23, 2020

Related U.S. Application Data

(63) Continuation-in-part of application No. 15/455,923, filed on Mar. 10, 2017, now Pat. No. 10,842,501.

(51) Int. Cl.
| | | |
|---|---|---|
| *A61B 50/31* | (2016.01) | |
| *A61B 17/132* | (2006.01) | |
| *A61B 50/30* | (2016.01) | |
| *A61B 50/00* | (2016.01) | |

(52) U.S. Cl.
CPC .......... *A61B 50/31* (2016.02); *A61B 17/1327* (2013.01); *A61B 2050/0085* (2016.02); *A61B 2050/3011* (2016.02); *A61B 2050/314* (2016.02)

(58) Field of Classification Search
CPC ................ A61B 50/31; A61B 17/1327; A61B 2050/0085; A61B 2050/3011; A61B 2050/314
USPC ......................................................... 224/663
See application file for complete search history.

(56) References Cited

U.S. PATENT DOCUMENTS

| | | | | |
|---|---|---|---|---|
| 4,140,164 | A * | 2/1979 | Staup ....................... | A45C 3/06 150/128 |
| 4,513,866 | A * | 4/1985 | Thomas ................... | A61F 17/00 190/110 |
| 4,799,923 | A * | 1/1989 | Campbell ............. | A61M 25/02 604/179 |
| 5,170,919 | A * | 12/1992 | DeSantis ............... | F41C 33/048 224/931 |
| 5,304,145 | A * | 4/1994 | Blair ..................... | A61M 25/02 604/179 |
| 5,403,285 | A * | 4/1995 | Roberts ................. | A61M 25/02 604/179 |
| 5,689,829 | A * | 11/1997 | Rose ...................... | A41D 27/20 2/77 |
| 5,692,237 | A * | 12/1997 | Bennett ................... | F41C 33/00 2/93 |
| 5,829,653 | A * | 11/1998 | Kaiser ...................... | F41H 5/08 2/2.5 |
| 6,131,198 | A * | 10/2000 | Westrick ............... | F41C 33/048 2/2.5 |
| 6,296,164 | B1 * | 10/2001 | Russo ................... | A61M 25/02 224/660 |
| 7,464,413 | B2 * | 12/2008 | Todd ...................... | A41D 27/20 2/94 |
| 7,712,645 | B2 * | 5/2010 | Calkin .................... | A61F 17/00 224/191 |

(Continued)

*Primary Examiner* — Peter N Helvey
(74) *Attorney, Agent, or Firm* — James E. Walton

(57) ABSTRACT

A system and method for rapidly accessing a tourniquet located in a pouch with a pull-away cover includes a tear-away cover. The tourniquet holder allows users to safely store in a fabric pouch a prepared tourniquet that is quickly accessible and coupled to a removable cover of the pouch. Users are able to fold the tourniquet in a manner that allows the tourniquet to be removed from the pouch and used nearly instantaneously.

7 Claims, 9 Drawing Sheets

(56) References Cited

U.S. PATENT DOCUMENTS

| | | | | |
|---|---|---|---|---|
| 8,032,951 | B1* | 10/2011 | Nestberg | A41D 27/20 |
| | | | | 2/69 |
| 8,328,058 | B2* | 12/2012 | Wilson | A45F 3/005 |
| | | | | 224/675 |
| 9,297,611 | B1* | 3/2016 | Roccisano | F41C 33/041 |
| 9,476,675 | B1* | 10/2016 | Manglos | F41C 33/0218 |
| 9,557,139 | B1* | 1/2017 | Miner | A44B 18/0073 |
| 2003/0182714 | A1* | 10/2003 | Mariland | A41D 13/0015 |
| | | | | 2/247 |
| 2007/0049871 | A1* | 3/2007 | Fleischer | A61M 25/02 |
| | | | | 604/180 |
| 2010/0083422 | A1* | 4/2010 | Lebl | A41D 27/20 |
| | | | | 2/251 |

* cited by examiner

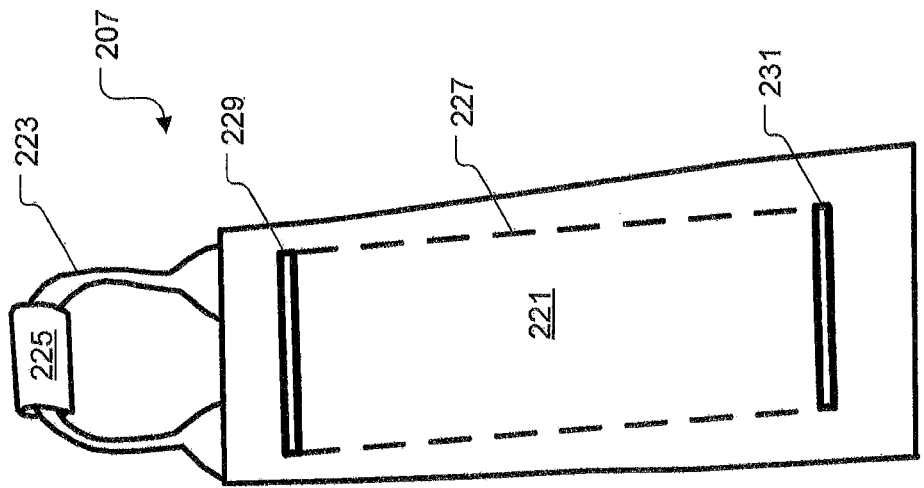
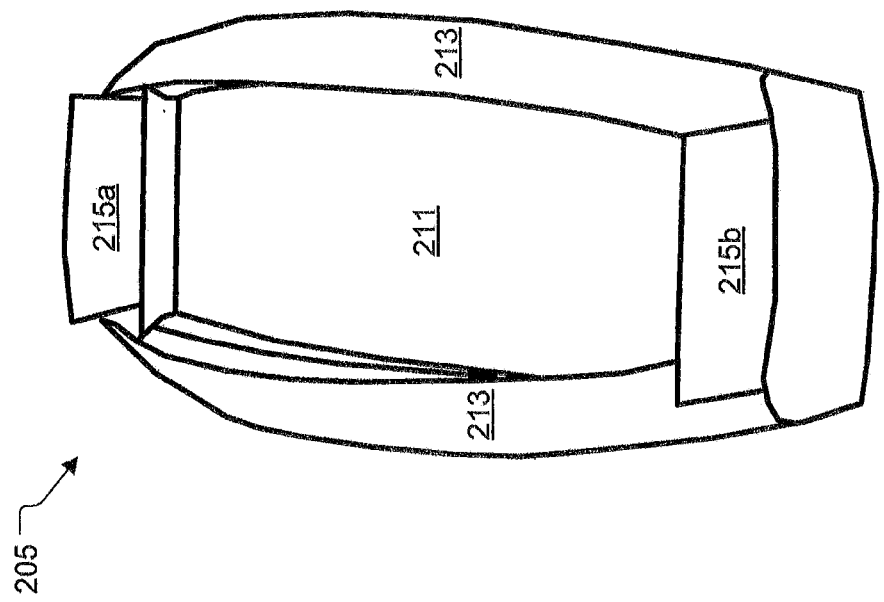

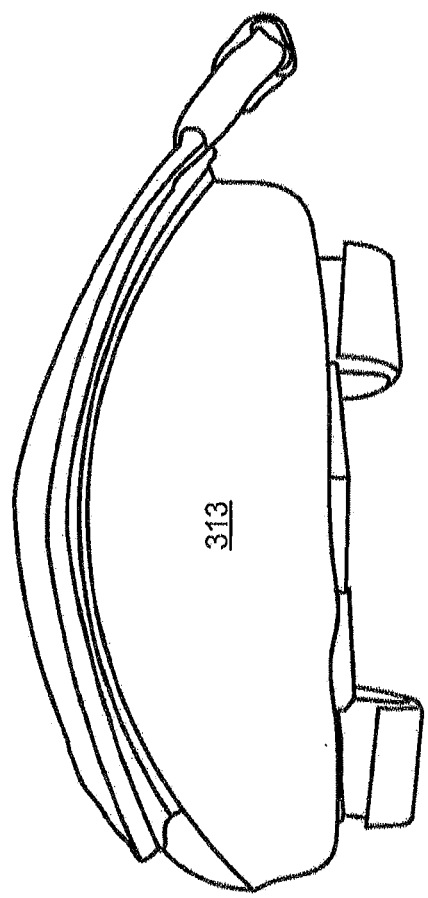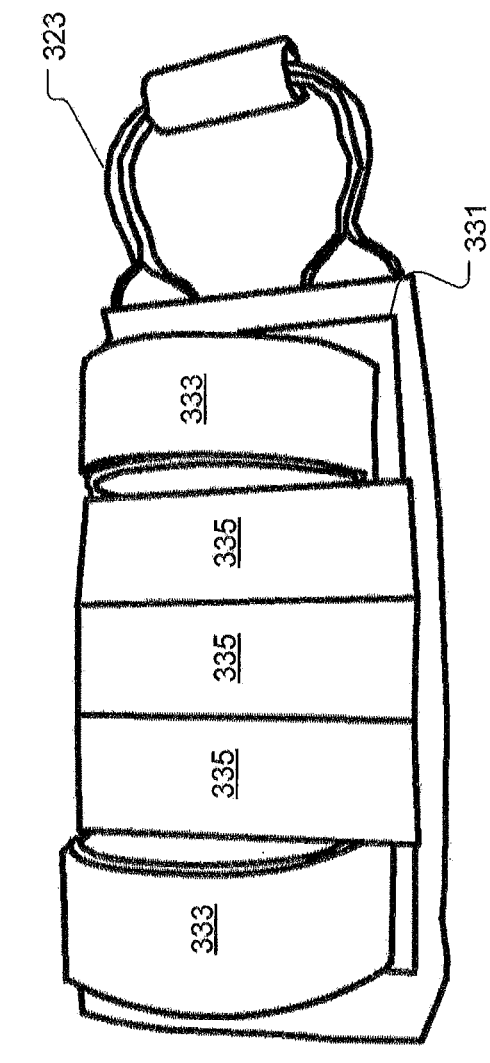

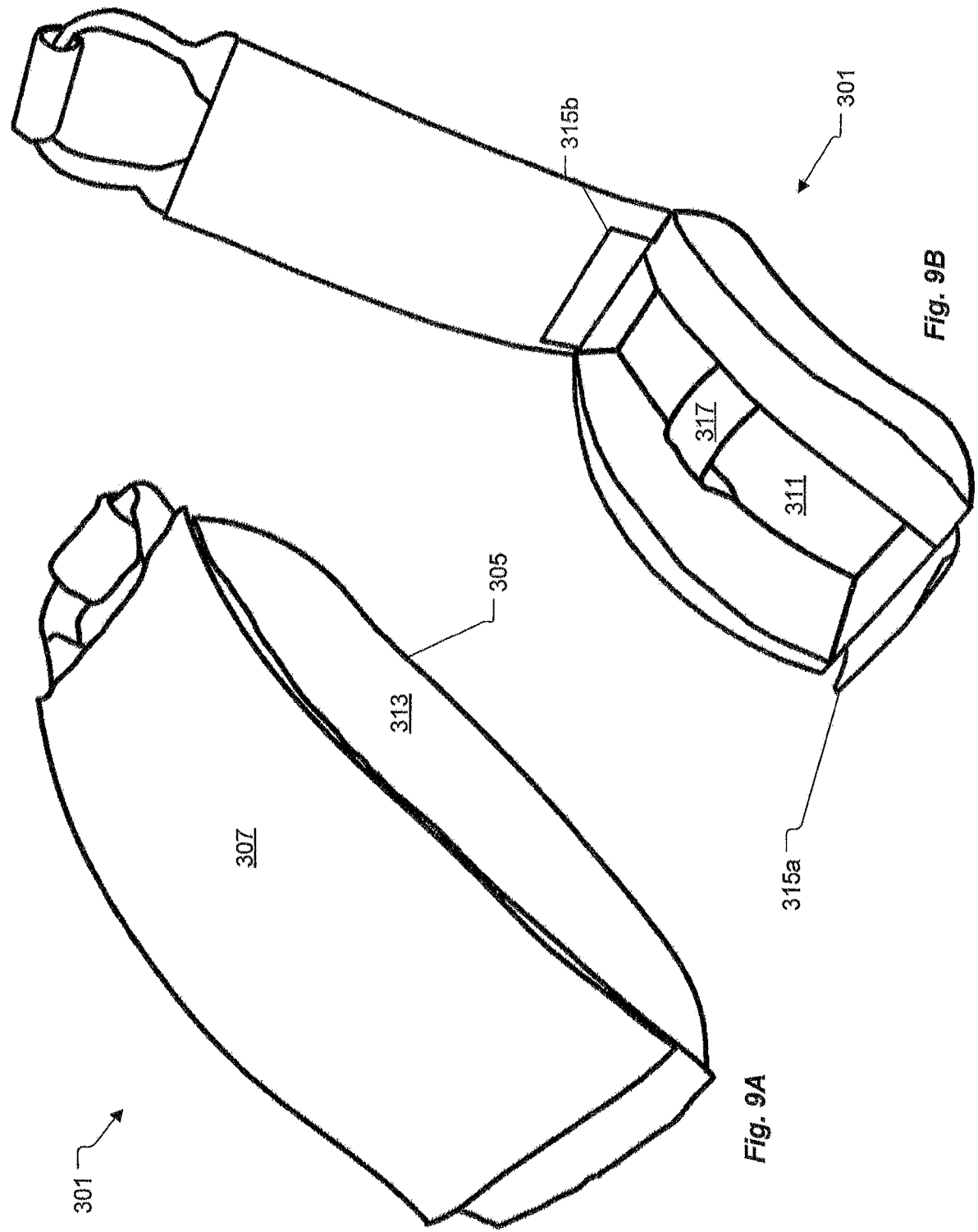

SYSTEM AND METHOD FOR RAPIDLY ACCESSING AN IMPROVED TOURNIQUET

This application is a continuation-in-part of U.S. application Ser. No. 15/455,923, filed on 10 Mar. 2017, titled "System and Method for Rapidly Accessing an Improved Tourniquet," which is incorporated herein by reference for all purposes.

BACKGROUND

1. Field of the Invention

The present invention relates generally to pouch for storing an improved tourniquet, and more specifically to a system and method for rapidly accessing a tourniquet.

2. Description of Related Art

Tourniquets are utilized to stop the flow of bleeding from trauma victims. Tourniquets conventionally are retained in an elongated holder with one end open much like a flashlight. However, tourniquets are not constructed like a flashlight and therefor a need exists for a tourniquet holder configured for the unique aspects of tourniquets as compared to flashlights. Thus, there exists significant room for improvement in the art for overcoming these and other shortcomings of conventional systems and methods for rapidly storing and accessing a tourniquet.

BRIEF DESCRIPTION OF THE DRAWINGS

The novel features believed characteristic of the system of the present application are set forth in the appended claims. However, the system itself, as well as a preferred mode of use, and further objectives and advantages thereof, will best be understood by reference to the following detailed description when read in conjunction with the accompanying drawings, in which the leftmost significant digit(s) in the reference numerals denote(s) the first figure in which the respective reference numerals appear, wherein:

FIG. 6A is a generally downward perspective view of a tourniquet pouch with a cover removed according to the present application;

FIG. 6B is a generally downward perspective view of a tourniquet pouch cover removed from the pouch according to the present application;

FIG. 8A is a generally side perspective view of a tourniquet pouch according to the present application;

FIG. 8B is a generally upward perspective view of a tourniquet pouch according to the present application;

FIG. 9A is a perspective view of a tourniquet pouch according to the present application; and FIG. 9B is a perspective view of an open tourniquet pouch according to the present application.

Figure 1:
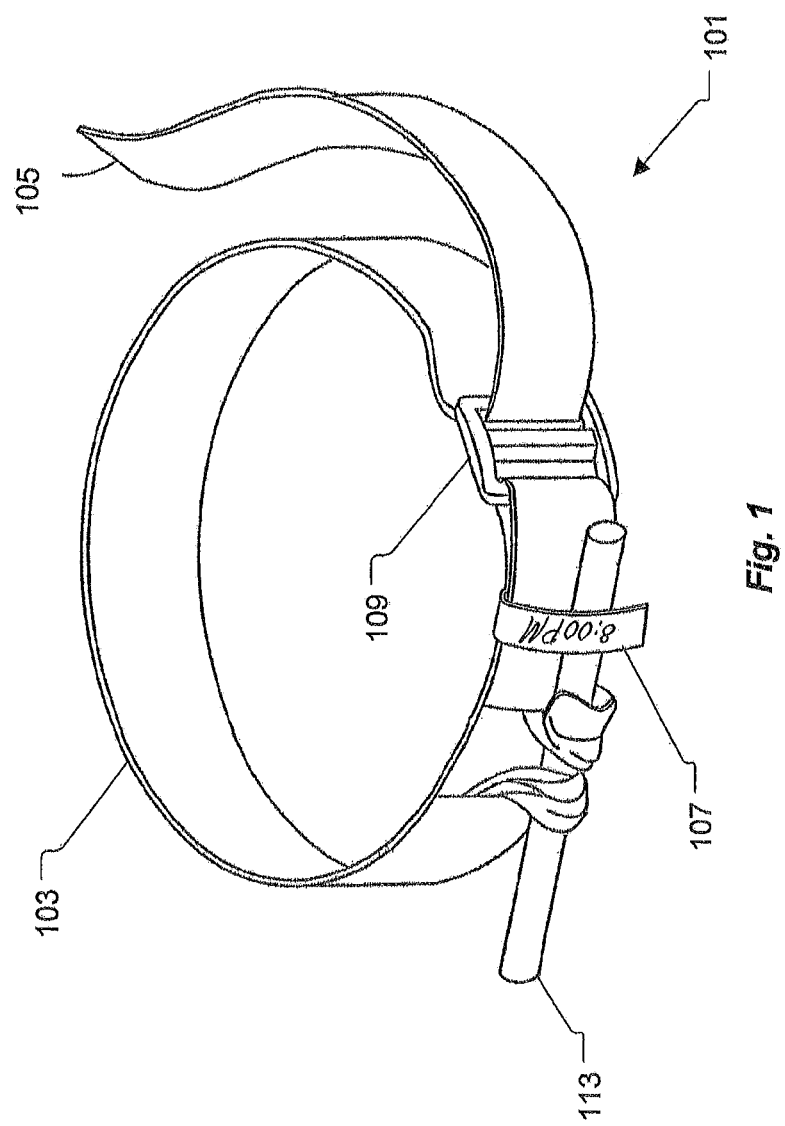
FIG. 1 is a perspective view of an improved tourniquet according to the present application.
Figure 2:
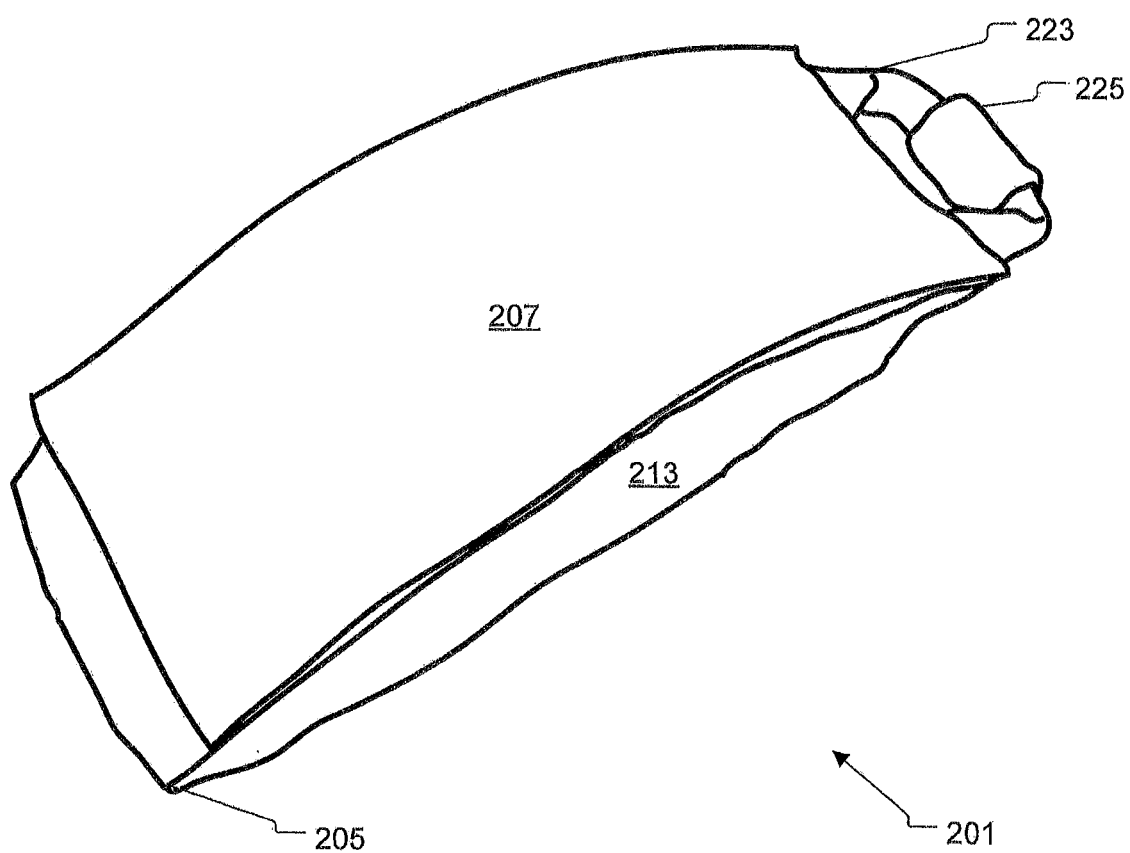
FIG. 2 is a perspective view of a tourniquet pouch according to the present application.
Figure 3:
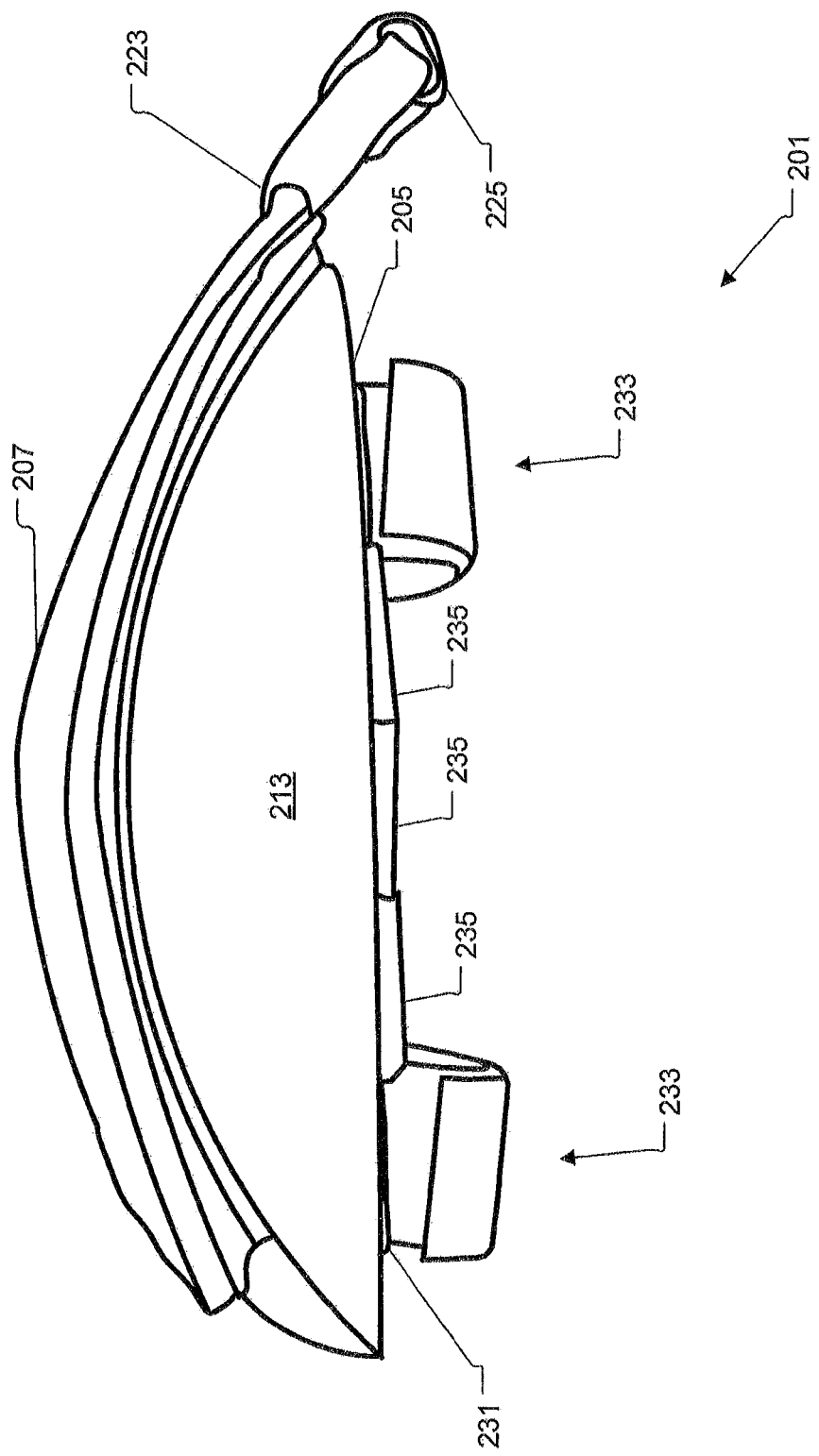
FIG. 3 is a generally side perspective view of a tourniquet pouch according to the present application.
Figure 4:
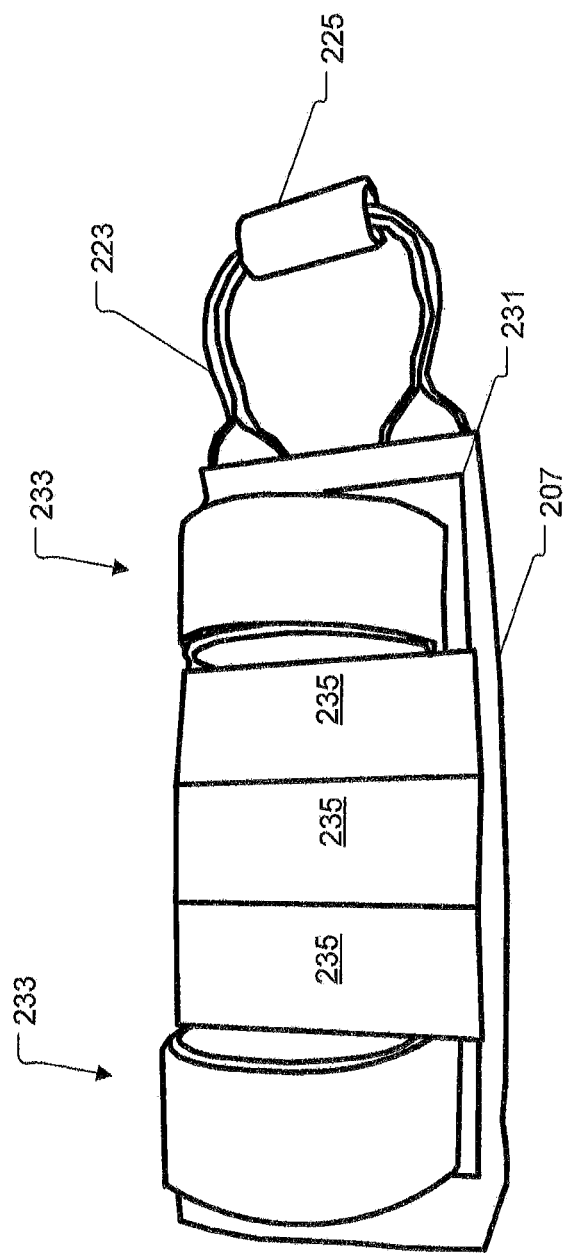
FIG. 4 is a generally upward perspective view of a tourniquet pouch according to the present application.
Figure 5:
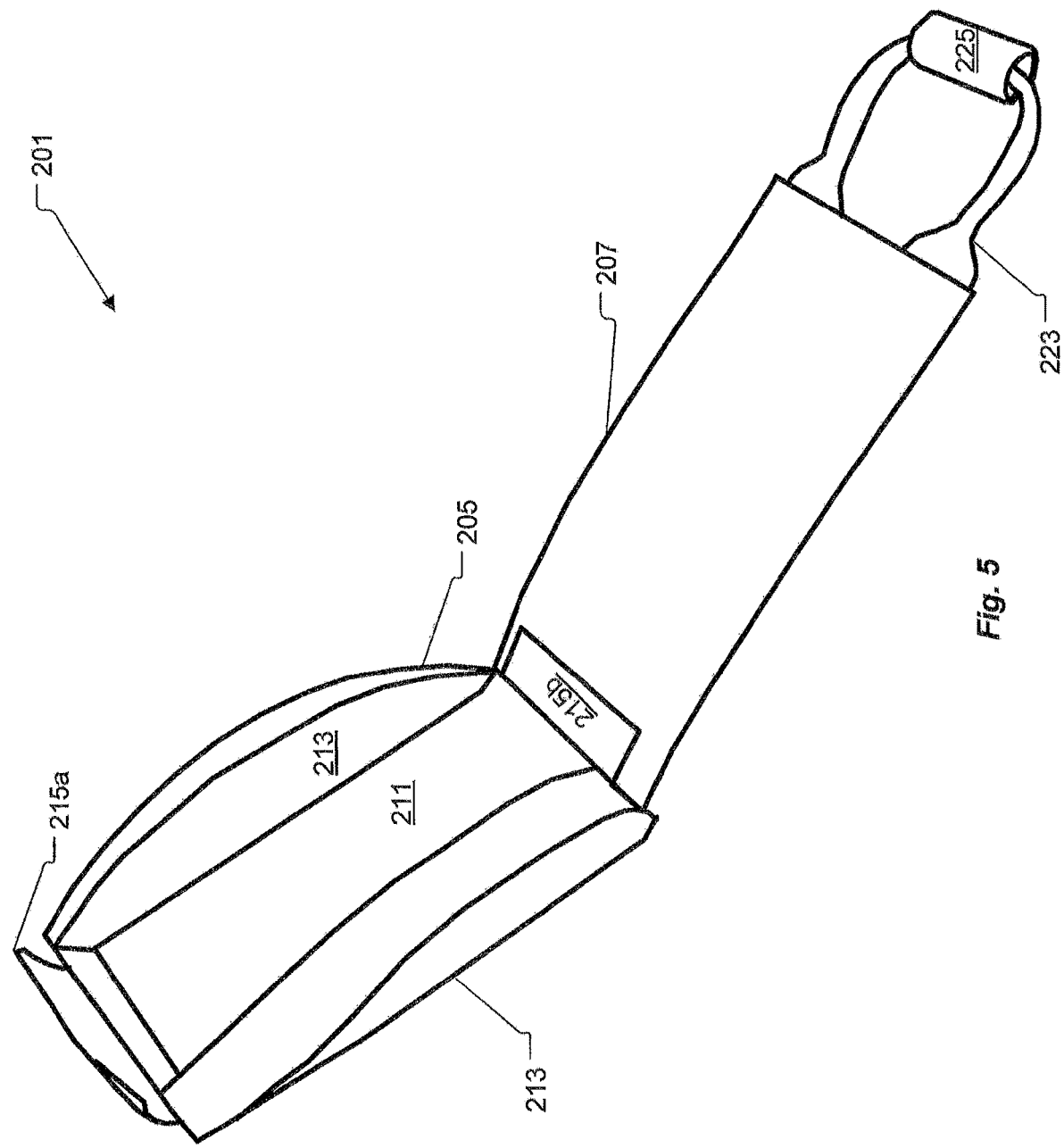
FIG. 5 is a perspective view of an open tourniquet pouch according to the present application.
Figure 7B:
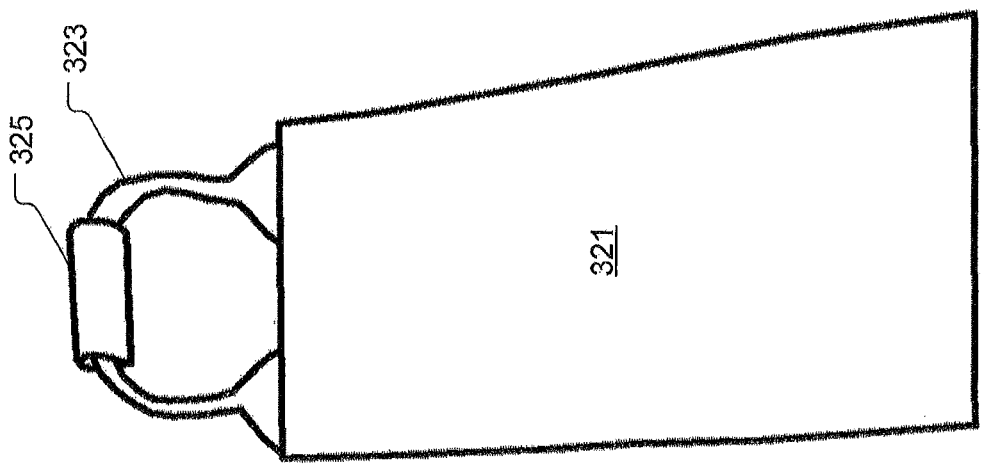
FIG. 7B is a generally downward perspective view of a tourniquet pouch cover removed from the pouch according to the present application.
Figure 7A:
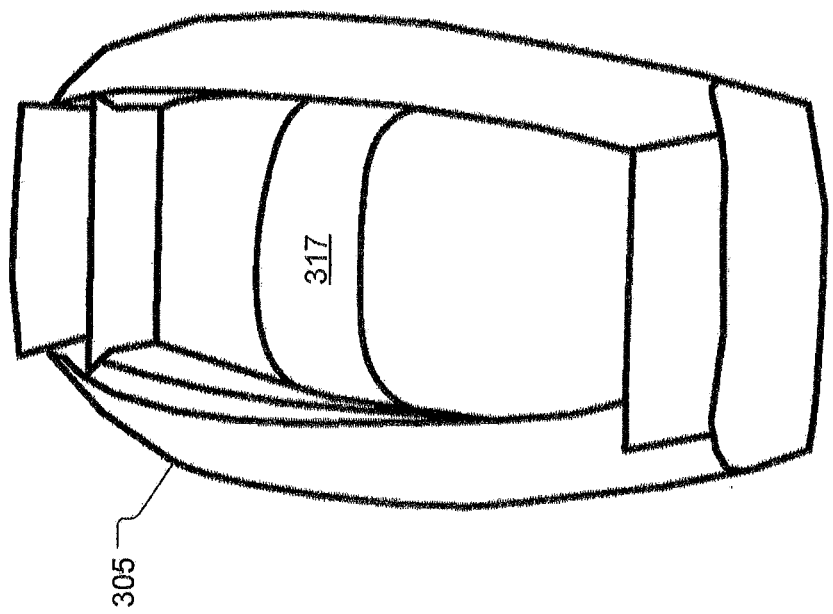
FIG. 7A is a generally downward perspective view of a tourniquet pouch with a cover removed according to the present application.

While the system of the present application is susceptible to various modifications and alternative forms, specific embodiments thereof have been shown by way of example in the drawings and are herein described in detail. It should be understood, however, that the description herein of specific embodiments is not intended to limit the method to the particular forms disclosed, but on the contrary, the intention is to cover all modifications, equivalents, and alternatives falling within the spirit and scope of the application as defined by the appended claims.

DETAILED DESCRIPTION OF THE PREFERRED EMBODIMENT

Illustrative embodiments of the system and method for rapidly accessing a tourniquet are provided below. It will of course be appreciated that in the development of any actual embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Tourniquets save lives by reducing bleeding in emergencies. The amount of time to apply a tourniquet directly relates to the amount of blood loss and therefore the likelihood that the injured victim will survive the trauma. The quicker the tourniquet is applied, the less blood is loss, the more likely the injured will make it. Therefore, an improved tourniquet holder that reduces the amount of time to extract the tourniquet from the holder will reduce blood loss and reduce the loss of life.

Referring now also to FIG. 1 in the drawings, a preferred embodiment of an improved tourniquet according to the present application is illustrated. Tourniquet 101 is comprised of a strap 103 having an adjustable diameter with a tail 105, a time label 107, a buckle 109, and a windlass 113 for removal of slack in the tourniquet. Tourniquet 101 is primarily fabric and as such is highly flexible. The flexibility of the tourniquet is preferred as device is configured to squeeze the injured limb to stop the flow of blood.

Referring now to FIGS. 2-6B in the drawings, a preferred embodiment of improved tourniquet pouch according to the present application is illustrated. Pouch 201 is comprised of a mounted member 205 and a cover 207. Mounted member 205 is comprised of a lower member 211, a first and a second elongated side members 213, and a first tab 215a and second tab 215b. Cover 207 is comprised of an elongated member 221, a first handle 223, and a tag 225. Cover 207 further comprises tabs and slots, such as slot 227. Slot 227 connects first opening 229 to second opening 231. Slot 227 is configured to retain the tail of the tourniquet while stored inside of pouch 201. While the preferred embodiment of the cover utilizes a first handle 223, it should be apparent that the cover alternatively further comprises a second handle opposite the first handle so the user can quickly remove the cover pulling either longitudinal direction relative to the pouch.

Side members 213 are preferably fixed to the opposing edges of lower member 211 by stitching; however, side members 213 may integral with lower member 211. Side members 213 are preferably arch shaped; however, other shapes may be used depending upon the shape, size, and volume desired within pouch 201. First tab 215a and second tab 215b are preferably fixed to the opposing ends of lower member 211 by stitching; however, first tab 215a and 215b may be integral with lower member 211.

Although pouch 201 is particularly well suited for storing and rapidly accessing tourniquet 101, it will be appreciated that pouch 210 may also provide storage and rapid access to various other medical devices, tools, survival gear, and any other type of equipment for which quick access is desirable.

In the preferred embodiment, the first and second elongated members 213 as well as the first and second tabs 215 are covered, at least partially, in hook tape. Additionally, an inner surface of the cover 207 is covered, at least partially, in loop tape. Preferably the loop tape of the cover is retained by the hook tape of the mounted member. The hook and loop tape is configured to provide a removable and replaceable interface between cover 207 and lower member 211. The first and second elongated members 213, as well as the first and second tabs 215, form a rectangular shaped opening that is covered by cover 207. With respect to the references herein to hook and loop tape, although the hook tape may be described as being on one component and the loop tape may be described as being on another component, it will be appreciated that the hook and loop tape may be applied in a vice versa fashion. In place of or in addition to the hook and loop tape, snaps and/or a plurality of magnets and magnetic materials can be used to allow cover 207 to be quickly removed in an emergency.

In the preferred embodiment the tourniquet is folded and coupled to cover 207 while stored in pouch 201. Upon use, cover 207 is removed from lower member 211, whereby tourniquet 101 is ready to be pulled away from cover 201 and utilized. Alternatively, tourniquet 101 may be stored entirely inside the pouch and removed by the user after cover 207 has been removed.

Pouch 201 is designed as a way to mount, store, and/or quickly deploy a tourniquet and/or other equipment. The following instructions may be used to use and deploy pouch 201. An included time label may be affixed to cover 207 as a supplement, but is not a replacement for the manufacturer's instructed specifications. With the sewn-in time label facing up, measure a 12-inch tail from the edge of the buckle to the end of tail 105 of tourniquet 101. Flip tourniquet 101 over, so that the 12-inch tail with the sewn-in time label is facing down. Remove cover 207 from lower member 211. Ensuring that the side of the tail 105 of tourniquet 101 with the sewn-in time label is still facing down, pass tail 105 through opening 229 closest to handle 223. Continue passing tail 105 through slot 227 until tail 105 exits opening 231. Pull back tail 105 until the end is coupled near the bottom channel opening by coupling the hook side of the tail to the loop side of the cover. The user then grasps tourniquet 101 at its natural fold with the buckle facing them and checks that tail 105 still measures 12 inches and that buckle 109 is securely fastened. Rotate tourniquet 101 to the backside, so that the windlass 113 is now facing the user. Twist windlass 113 up and to the right to fold the nylon strap, aligning windlass 113 in a vertical orientation along the tourniquet body. Rotate tourniquet 101 back to the front side with buckle 109 facing towards the user. The user, while holding the tourniquet body and windlass 113, grasps the remaining strap and 207 cover in opposite hand. From the bottom, fold strap and cover 207 up and behind the tourniquet body and windlass 113.

The user continues to fold the strap and cover 207 over and on top of the tourniquet buckle. Cover 207 should now be facing the user with an outer surface of cover 207 visible to the user. The user then tucks the loose strap loop upwards into the small void underneath tourniquet buckle 209. Grasping the pouch, and ensuring the first tab is oriented towards the top. Orient the bottom channel opening of the pouch cover to the bottom of the pouch body and lift tourniquet tail to expose interior loop. Affix the prepared pouch cover to the second tab 215b at the bottom of lower member 211. Fold pouch cover 207 and tourniquet 101 into pouch body. Adhere cover 207 to pouch body side attachment tabs 213 one at a time, ensuring top remains open. Before securing cover 207 to the first tab 215a, ensure tourniquet windlass 113 is out of the way by pressing it down into the pouch. Secure cover 207 to first tab 215a. Pouch 201 is now loaded and ready for deployment.

To deploy, pull outward on handle 223 away from the pouch body, exposing tourniquet 101. The user then follows tourniquet manufacturer's instructions for application to the appendage.

Pouch 201 further includes a unique four-way mounting system 231. Mounting system 231 includes at least four different types of mounts, including: (1) a plurality of malice clip straps configured to retain a malice clip; (2) at least one wrap-around adjustable strap; (3) a first pass-through mount passing between the malice clip straps and the lower member in a first direction; and (4) a second pass-through mount passing between the malice clip straps and the lower member in a second direction. Narrow ends of the mounting system 231 are attached to the mounted member 205 typically through sewing however other attachments are contemplated by this application such as fusing, bonding, and welding. Mounting system 231 further comprises a first and a second adjustable strap 233, and a plurality of fixed diameter straps 235. Mounting system 231 is configured to allow a user to mount the pouch at least four different ways. First, the user can attach the pouch 201 to a backpack by wrapping the first and second adjustable straps around the backpack's shoulder straps. Second, the user can mount the pouch horizontal on a belt by inserting the belt through the plurality of fixed diameter straps 235. Third, the user can mount the pouch 201 vertically on a belt by inserting the belt between the mounting system 231 and the mounted member 205. Fourth, the user can couple the pouch 201 to a MOLLE based attachment area with the use of Malice clips. Alternatively the pouch can be sewed directly to the surface of the user's clothing or backpack and is not removable.

FIG. 6A illustrates pouch 201 with cover 207 removed. Any contents stored inside of pouch 201 is readily available, because cover 207 is removed. Unlike conventional tourniquet holders, pouch 201 does not require the user to yank the tourniquet out of a small opening.

Referring now to FIGS. 7A-9B in the drawings, an alternative embodiment of improved tourniquet pouch according to the present application is illustrated. Pouch 301 as compared to pouch 201 utilizes additional material to store more inside. Furthermore, the height, width, and depth of the pouch 301, as compared to pouch 201, are larger. Pouch 301 is comprised of a mounted member 305 and a cover 307. Mounted member 205 is comprised of a lower member 311, a first and a second elongated side members 313, a first tab 315a and second tab 315b, and an elastic retention strap 317. Cover 307 is comprised of an elongated member 321, a first handle 323, and a tag 325. While the preferred embodiment of the cover utilizes a first handle 323, it should be apparent that the cover alternatively further comprises a second handle opposite the first handle so the user can quickly remove the cover pulling either longitudinal direction relative to the pouch.

Pouch 301 further comprised a mounting system 331. Pouch 301 also includes a four-way mounting system 331. Mounting system 331 includes at least four different types of mounts, including: (1) a plurality of malice clip straps configured to retain a malice clip; (2) at least one wrap-around adjustable strap; (3) a first pass-through mount passing between the malice clip straps and the lower member in a first direction; and (4) a second pass-through mount passing between the malice clip straps and the lower member in a second direction. The ends of mounting system 331 are attached to the lower member 305 typically through sewing however other attachments are contemplated by this application such as fusing, bonding, and welding. Mounting system 331 includes at least one, but preferably two, adjustable straps 333. Mounting system 331 includes a plurality of fixed diameter straps, or malice clip straps 335, which are sized, shaped and configured to retain a malice clip. Mounting system 331 includes a first pass-through mount that is formed by a longitudinal slot between lower member 305 and malice clip straps 335; and a second pass-through mount that is formed by a transverse slot between lower member 305 and malice clip straps 335

Mounting system 331 is configured to allow a user to mount the pouch at least four different ways. First, the user can attach pouch 301 to a backpack by wrapping first and second adjustable straps 333 around the shoulder straps of a backpack. Second, the user can mount pouch 301 horizontally on a belt by inserting the belt through the first pass-through mount. Third, the user can mount the pouch 301 vertically on a belt by inserting the belt though the second pass-through mount. Fourth, the user can couple the pouch 301 to a MOLLE based attachment area with the use of malice clips via the malice clip straps. Alternatively the pouch can be sewed directly to the surface of the user's clothing or backpack and is not removable.

It is apparent that a system with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

The invention claimed is:

1. A holder for rapidly accessing equipment, the holder comprising:
    a lower member having a first edge, an opposing second edge, a first end, and an opposing second end;
    a first side member attached to the first edge of the lower member;
    a second side member attached to the second edge of the lower member;
    a first tab attached to the first end of the lower member;
    a second tab attached to the second end of the lower member;
    a rapid-release cover releasably coupled to the first side member, the second side member, the first tab, and the second tab;
    at least one retention mechanism coupled to the cover for releasably retaining the equipment; and
    a four-way mounting system coupled to the lower member, the four-way mounting system comprising:
        a plurality of malice clip straps configured to retain a malice clip;
        at least one wrap-around adjustable strap;
        a first pass-through mount passing between the malice clip straps and the lower member in a first direction; and
        a second pass-through mount passing between the malice clip straps and the lower member in a first direction.

2. The holder according to claim 1, wherein the equipment is fully enclosed between the lower member and the cover.

3. The holder according to claim 1, further comprising:
    a handle located on one end of the cover.

4. The holder according to claim 1, wherein the retention mechanism comprises:
    a slot disposed in the cover.

5. The holder according to claim 1, wherein the retention mechanism comprises:
    an elastic retention strap disposed at least partially inside the pouch.

6. The holder according to claim 1, wherein the first side member and the second side member are arch shaped.

7. The holder according to claim 1, wherein the rapid-release cover is releasably coupled to the first side member, the second side member, the first tab, and the second tab via hook and loop tape.

* * * * *